United States Patent
Liu et al.

(10) Patent No.: US 10,531,687 B2
(45) Date of Patent: Jan. 14, 2020

(54) ULTRASONIC ATOMIZER AND ELECTRONIC CIGARETTE

(71) Applicant: CHINA TOBACCO HUNAN INDUSTRIAL CO., LTD., Changsha, Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Jianhua Yi, Hunan (CN); Hong Yu, Hunan (CN); Yang Wang, Hunan (CN); Youlin He, Hunan (CN)

(73) Assignee: CHINA TOBACCO HUNAN INDUSTRIAL CO., LTD., Changsha, Hunan (CN)

( * ) Notice: Subject to any disclaimer, the term of this patent is extended or adjusted under 35 U.S.C. 154(b) by 176 days.

(21) Appl. No.: 15/578,561

(22) PCT Filed: Jun. 22, 2016

(86) PCT No.: PCT/CN2016/086673
§ 371 (c)(1),
(2) Date: Nov. 30, 2017

(87) PCT Pub. No.: WO2017/197703
PCT Pub. Date: Nov. 23, 2017

(65) Prior Publication Data
US 2018/0153217 A1    Jun. 7, 2018

(30) Foreign Application Priority Data

May 16, 2016  (CN) .................. 2016 2 04463153 A

(51) Int. Cl.
A24F 13/00    (2006.01)
A24F 47/00    (2006.01)
A61M 15/06    (2006.01)

(52) U.S. Cl.
CPC .......... *A24F 47/008* (2013.01); *A24F 47/002* (2013.01); *A61M 15/06* (2013.01)

(58) Field of Classification Search
CPC ...................................................... A24F 47/00
(Continued)

(56) References Cited

U.S. PATENT DOCUMENTS

2018/0242644 A1*  8/2018  Bessant ................ H05B 1/0227

FOREIGN PATENT DOCUMENTS

| CN | 2889333 Y | 4/2007 |
| CN | 202233005 U | 5/2012 |

(Continued)

OTHER PUBLICATIONS

International Search Report issued in International Application No. PCT/CN2016/086673 dated Feb. 17, 2017, 4 pages.

*Primary Examiner* — Phuong K Dinh
(74) *Attorney, Agent, or Firm* — Mauriel Kapouytian Woods LLP; James Woods

(57) ABSTRACT

Embodiments of the present invention disclose an ultrasonic atomizer and electronic cigarette. The ultrasonic atomizer comprises a liquid storage cavity and a piezoelectric ceramic piece both are provided in an outer sleeve the plane where the piezoelectric ceramic piece is located is parallel to the axial line of the outer sleeve; at least one surface of the piezoelectric ceramic piece is in contact with a liquid storage body; the liquid storage body communicates with the liquid storage cavity; and an atomization surface of the piezoelectric ceramic piece communicates with an air passage.

17 Claims, 7 Drawing Sheets

(58) Field of Classification Search
USPC .................................................. 131/328–329
See application file for complete search history.

(56) References Cited

FOREIGN PATENT DOCUMENTS

| CN | 102655773 A | 9/2012 |
| CN | 105559151 A | 5/2016 |
| CN | 105768238 A | 7/2016 |
| EP | 2 608 686 B1 | 6/2015 |
| KR | 200470732 Y1 | 1/2014 |

* cited by examiner

//ULTRASONIC ATOMIZER AND ELECTRONIC CIGARETTE

CROSS-REFERENCE TO RELATED APPLICATIONS

This application is a national phase application of international application number PCT/CN2016/086673 filed on Jun. 22, 2016, which claims priority to Chinese application number 2016204463153 filed on May 16, 2016. The entire contents of these applications are hereby incorporated herein by reference.

FIELD OF INVENTION

The present invention relates to an ultrasonic atomizer and electronic cigarette.

BACKGROUND OF THE INVENTION

The existing atomizers of electronic cigarette generally adopt heating wires to heat tobacco tar in tobacco tar storage cotton, the temperatures of the heating wires are relatively high in a heating process, so the heating wires are scorched easily and produce the smell of burnt food, moreover the high temperatures produced by the heating wires are transferred to outer walls of the atomizers easily, so that the electronic cigarette becomes hot, the energy efficiency is low, the smoking taste is poor, and meanwhile the atomizers are prone to tobacco tar leakage.

BRIEF SUMMARY OF THE INVENTION

The technical problem to be solved in the present invention is to provide an ultrasonic atomizer and electronic cigarette in view of the shortcomings of the prior art.

To solve the above technical problem, the present invention adopts the technical solutions as follows: an ultrasonic atomizer, comprising a liquid storage cavity, an ultrasonic oscillation component, an air passage provided in an outer sleeve, and an electrode electrically connected with an external power supply for driving oscillation of the piezoelectric ceramic piece; the ultrasonic oscillation component comprises the piezoelectric ceramic piece and a liquid storage body; the piezoelectric ceramic piece is provided to extend along the longitudinal direction of the ultrasonic atomizer, so that when the ultrasonic atomizer is vertically placed, the piezoelectric ceramic piece is in a vertical state; at least one surface of the piezoelectric ceramic piece is in contact with the liquid storage body; the liquid storage body communicates with the liquid storage cavity and is used for adsorbing liquid in the liquid storage cavity; and the liquid storage body communicates with the air passage, so that after the piezoelectric ceramic piece atomizes the liquid in the liquid storage body, steam fog is exhausted from the air passage.

The liquid storage body is located on one surface of the piezoelectric ceramic piece, and one surface of the liquid storage body which is deviated from the piezoelectric ceramic piece communicates with the air passage.

The liquid storage body is made of a tobacco tar absorption material and is of platy structure, and the liquid storage body is covered on the piezoelectric ceramic piece.

The liquid storage body transfers liquid to the piezoelectric ceramic piece to be atomized, and the working life of the piezoelectric ceramic piece is prolonged.

In a preferred solution of the present invention, the liquid storage cavity and the piezoelectric ceramic piece are provided side by side, the ultrasonic atomizer further comprises a side cover; and the side cover is covered on one side of the outer sleeve; an accommodation cavity is provided in the side cover; and the piezoelectric ceramic piece is provided in the accommodation cavity to fix the piezoelectric ceramic piece, and thus the influence of the vibration of the piezoelectric ceramic piece on the atomization effect can be prevented.

The ultrasonic atomizer further comprises a bracket and a fixing base, a cavity used for accommodating the ultrasonic oscillation component is provided on the fixing base, the ultrasonic oscillation component is fixed in the fixing base, the fixing base is embedded in the accommodation cavity through the bracket, and the bracket is fixed between the fixing base and the side cover, so that loosening of the piezoelectric ceramic piece can be prevented, and the internal structure of the atomizer is more compact and stable.

A first vent groove is provided in the bracket, a second vent groove is provided in the fixing base, and both of the first vent groove and the second vent groove communicate with the surface of the liquid storage body which is deviated from the piezoelectric ceramic piece, so that after the piezoelectric ceramic piece atomizes liquid in the liquid storage body, steam fog is exhausted from the first vent groove and/or the second vent groove.

In another preferred solution of the present invention, the piezoelectric ceramic piece is provided above the liquid storage cavity, both sides of the piezoelectric ceramic piece communicate with the air passage, both sides of the piezoelectric ceramic piece are in contact with the liquid storage body, and the surface of the liquid storage body which is deviated from the piezoelectric ceramic piece communicates with the air passage. The liquid storage cavity is provided below the piezoelectric ceramic piece, thereby effectively solving the problem of slow start of the atomizer resulting from the accumulation of excessive liquid on the piezoelectric ceramic piece.

An elastic mounting sleeve is provided in the outer sleeve; an accommodation groove for accommodating the piezoelectric ceramic piece is provided in the elastic mounting sleeve, and the wall of the accommodation groove elastically props against the piezoelectric ceramic piece and the liquid storage body. Thus, influence of the shake of the piezoelectric ceramic piece on the atomization effect can be prevented, and the piezoelectric ceramic piece can be more stable.

One end of the liquid storage body which is away from the suction nozzle is inserted in the liquid storage cavity. When the atomizer is used, the liquid is absorbed onto the entire liquid storage body from the lower end of the liquid storage body, that is, the liquid is permeated into the liquid storage body against to the gravity direction so as to prevent the slow start of the atomizer resulting from the accumulation of excessive liquid on the piezoelectric ceramic piece.

A first outer cover and a second outer cover for fixing the piezoelectric ceramic piece are respectively provided on one side and the other side of the elastic mounting sleeve; and vent grooves communicating with the air passage are provided in both of the first outer cover and the second outer cover, and the vent grooves respectively communicate with the air passage on one side and the other side of the piezoelectric ceramic piece. Therefore, the steam fog formed by atomizing the liquid on both surfaces of the piezoelectric ceramic piece enters the air passage along the vent grooves to be mixed, the amount of the steam fog can be further increased, the smoking taste can also be improved, and thus the user experience is enhanced.

A first through hole is provided in the middle of the first outer cover, a fixing groove is provided in one surface of the second outer cover which is faced to the first outer cover, the piezoelectric ceramic piece is provided in the fixing groove, and a second through hole is provided in the wall of the fixing groove which is faced to the first through hole; and the first through hole and the second through hole are respectively provided on one side and the other side of the piezoelectric ceramic piece and both of them communicate with the air passage through the vent grooves.

Sealing pads are provided on the surface of the first outer cover and on the surface of the second outer cover which are deviated from the piezoelectric ceramic piece, and gaps are provided between the sealing pads and the surface of the liquid storage body which is deviated from the piezoelectric ceramic piece, so that the sealing pads neither block the first through hole nor block the second through hole, and thus the steam fog is guaranteed to be taken away smoothly, and the user experience is enhanced.

One end of the outer sleeve is connected with a suction nozzle, and the suction nozzle communicates with the air passage. Thus, in a smoking process, the smoke is inhaled to the oral cavity of the user through the suction nozzle, and thus the smoking demand of the user can be satisfied.

Correspondingly, the present invention further provides an electronic cigarette, including the above-mentioned ultrasonic atomizer and a power supply component for providing a working power supply for the ultrasonic atomizer; and the bottom end of outer sleeve of the ultrasonic atomizer is in screw joint, plug connection or magnetic connection with the power supply component.

Compared with the prior art, the present invention has the following beneficial effects: the present invention has simple structure and atomizes tobacco tar and other liquid using the principle of ultrasonic wave, thereby solving the problem that the existing electronic cigarette has poor taste because it is liable to produce burnt flavor; the energy efficiency is high; as the piezoelectric ceramic piece is vertically provided in the outer sleeve of the atomizer, the problems can be effectively solved that start of the piezoelectric ceramic piece in the atomizer is slow and small amount of smoke resulting from the accumulation of excessive liquid on the atomization surface of the piezoelectric ceramic piece, and the problem that the existing atomizer of electronic cigarette is prone to tobacco tar leakage is also solved.

BRIEF DESCRIPTION OF THE SEVERAL VIEWS OF THE DRAWING(S)

DETAILED DESCRIPTION OF THE INVENTION

Figure 1:
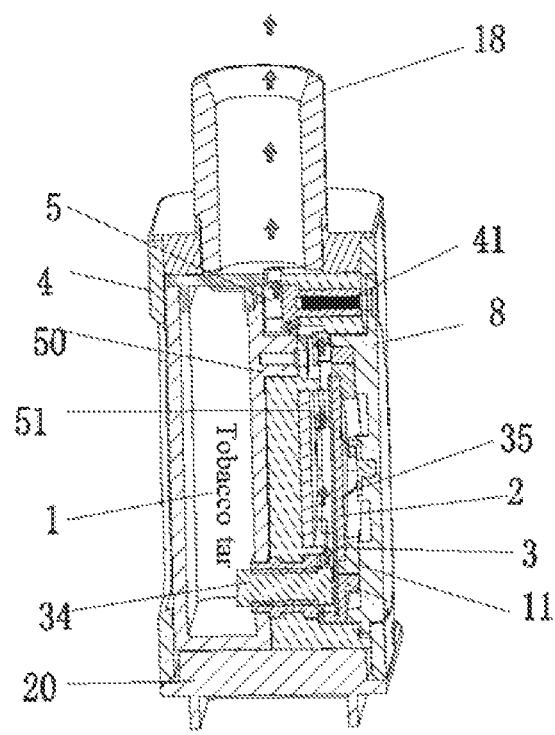
FIG. 1 is a structural schematic diagram of embodiment 1 of the present invention.

As shown in FIG. 1, an atomizer in embodiment 1 of the present invention comprises a liquid storage cavity 1, an ultrasonic oscillation component 2 and an air passage 5 both provided in an outer sleeve 4, and an electrode 17 electrically connected with an external power supply for driving oscillation of a piezoelectric ceramic piece 21; the ultrasonic oscillation component 2 is provided to extend along the longitudinal direction of the ultrasonic atomizer, so that when the ultrasonic atomizer is vertically placed, the piezoelectric ceramic piece 21 is in a vertical state (i.e., the piezoelectric ceramic piece 21 is vertically provided in the outer sleeve 4); one surface of the piezoelectric ceramic piece 21 is in contact with the liquid storage body 3 (tobacco tar storage cotton); the liquid storage body 3 communicates with the liquid storage cavity 1; and the liquid storage body 3 communicates with the air passage 5, so that after the piezoelectric ceramic piece 21 atomizes the liquid in the liquid storage body 3, steam fog is exhausted from the air passage 5.

In the present invention, both surfaces of the piezoelectric ceramic piece 21 can be atomization surfaces (i.e., surfaces which are oscillated to atomize the liquid), and the piezoelectric ceramic piece is a solid piezoelectric ceramic piece, that is to say, no hole is provided in the surfaces of the piezoelectric ceramic piece, and thus the liquid cannot penetrate through the piezoelectric ceramic piece.

In the present invention, to guarantee the smoke yield and to quickly start the piezoelectric ceramic piece to atomize the liquid in the liquid storage body, the thickness of the liquid storage body is set as 0.05-2.5 mm.

In the embodiment 1 of the present invention, the liquid storage body 1 and the piezoelectric ceramic piece 21 are provided side by side.

As shown in FIG. 1, in embodiment 1, a top end (one end that is close to a suction nozzle 18) of a side cover 8 is in fixed connection with the top end of the outer sleeve through a nut 41. When maintenance is required, an atomization core part can be detached, thereby being convenient for replacement.

Figure 2:
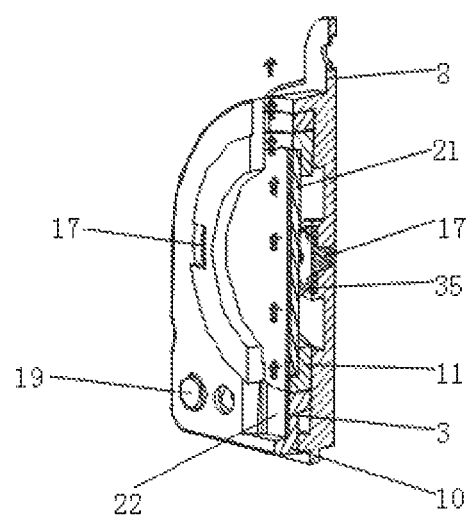
FIG. 2 is a structural schematic diagram of an atomization core in embodiment 1 of the present invention.
Figure 3:
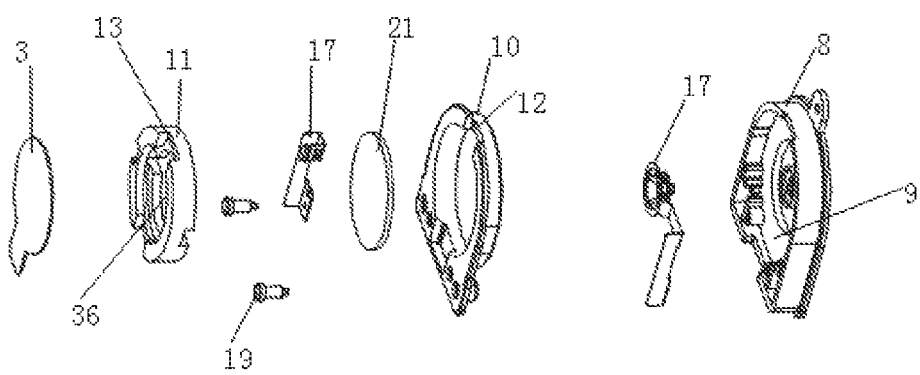
FIG. 3 is an explosive view of the atomization core in embodiment 1 of the present invention.

As shown in FIG. 2 and FIG. 3, the atomization core part comprises the side cover 8 provided in the outer sleeve 4; an accommodation cavity 9 is provided in the side cover 8; and the piezoelectric ceramic piece 21 is fixed to the upper part of a bracket 10, the upper part of the bracket 10 is fixed in the accommodation cavity 9, and the bracket 10 is fixed between a fixing base 11 and the side cover 8; a first vent groove 12 is provided in the bracket 10, a second vent groove 13 is provided in the fixing base 11, both of the first vent groove 12 and the second vent groove 13 communicate with the atomization surface of the piezoelectric ceramic piece 21, the first vent groove 12 communicates with the second vent groove 13, so that the flow of the smoke can be more smooth and has higher speed; and both sides of the piezoelectric ceramic piece 21 are respectively in contact with an electrode 17. A cavity 36 used for accommodating the liquid storage body 3 and the piezoelectric ceramic piece 21 is provided in the fixing base 11.

As shown in FIG. 1, a first gap is provided between a thermal insulation layer 51 and the atomization core, the first vent groove 12 and the second vent groove 13 are connected with the first gap after the first vent groove 12 and the second vent groove 13 are communicated with each other, a second gap is provided between the top end of the side cover 8 and a big bracket 50, and the first gap communicates with the second gap to form the air passage 5.

In the embodiment 1, as shown in FIG. 2 and FIG. 3, a mounting hole 22 is provided in the bottom of the bracket 10, a tobacco tar guide rope 34 passes through the mounting hole 22, the upper section of the liquid storage body is a circle with a bulge, and the bulge is in contact with the tobacco tar guide rope, so that the tobacco tar can be guided into the liquid storage body from the tobacco tar guide rope.

One end of the tobacco tar guide rope stretches into the liquid storage cavity 1 from the bottom end (one end that is away from the suction nozzle) of the liquid storage cavity 1, and the other end of the tobacco tar guide rope is in contact with the bottom (one end that is away from the suction nozzle) of the liquid storage body 3 to guide the tobacco tar into the liquid storage body.

An elastic piece 35 is provided between the electrode 17 and the piezoelectric ceramic piece 21 to further guarantee good electric contact.

A sealing pad 25 can be provided between the piezoelectric ceramic piece 21 and the side cover 8, and the sealing pad 25 is made of silica gel which has elasticity, so that the piezoelectric ceramic piece can be further protected from being damaged in an oscillation process.

To further guarantee good electric contact, a spring electrode 19 which is in fastened connection with the bracket 10 and the side cover 8 is adopted in the present invention.

In the present invention, the fixing base 11 is a silica gel base to prevent the piezoelectric ceramic piece from being damaged in the oscillation process.

The top end (one end of a gas outflow direction) of the outer sleeve 4 is connected with the suction nozzle 18, and the suction nozzle 18 communicates with the air passage 5; and the bottom end of the outer sleeve 4 is in fixed connection with a bottom cover 20.

Figure 4:
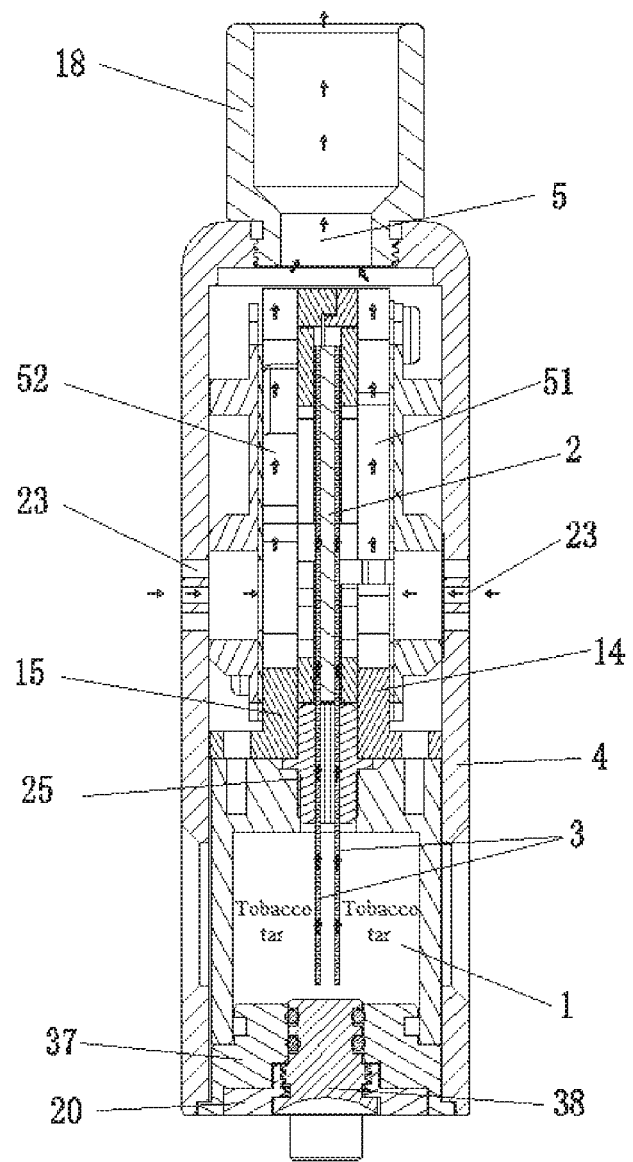
FIG. 4 is a structural schematic diagram of embodiment 2 of the present invention.

As shown in FIG. 4, in embodiment 2 of the present invention, the liquid storage cavity 1 of the atomizer is provided below the piezoelectric ceramic piece 21, both sides of the piezoelectric ceramic piece 21 are in contact with the liquid storage body 3, one end of the liquid storage body 3 stretches into the liquid storage cavity 1 to contact with the liquid, so that the liquid storage body 3 transfers the liquid in the liquid storage cavity 1 to the both sides of the piezoelectric ceramic piece 21 using its own adsorption force so as to enable the piezoelectric ceramic piece 21 to atomize the liquid.

A first vent passage 51 and a second vent passage 52 respectively communicates with one side and the other side of the piezoelectric ceramic piece 21, both of the first vent passage 51 and the second vent passage 52 communicate with the air passage 5 along the airflow direction, that is, the smoke in the first vent passage 51 and the second vent passage 52 is gathered to the air passage 5, so that more intense smoke can be provided to the user; and air inlet holes 23 communicated with the first vent passage 51 and the second vent passage 52 are provided in two sides of the outer sleeve 4.

Figure 5:
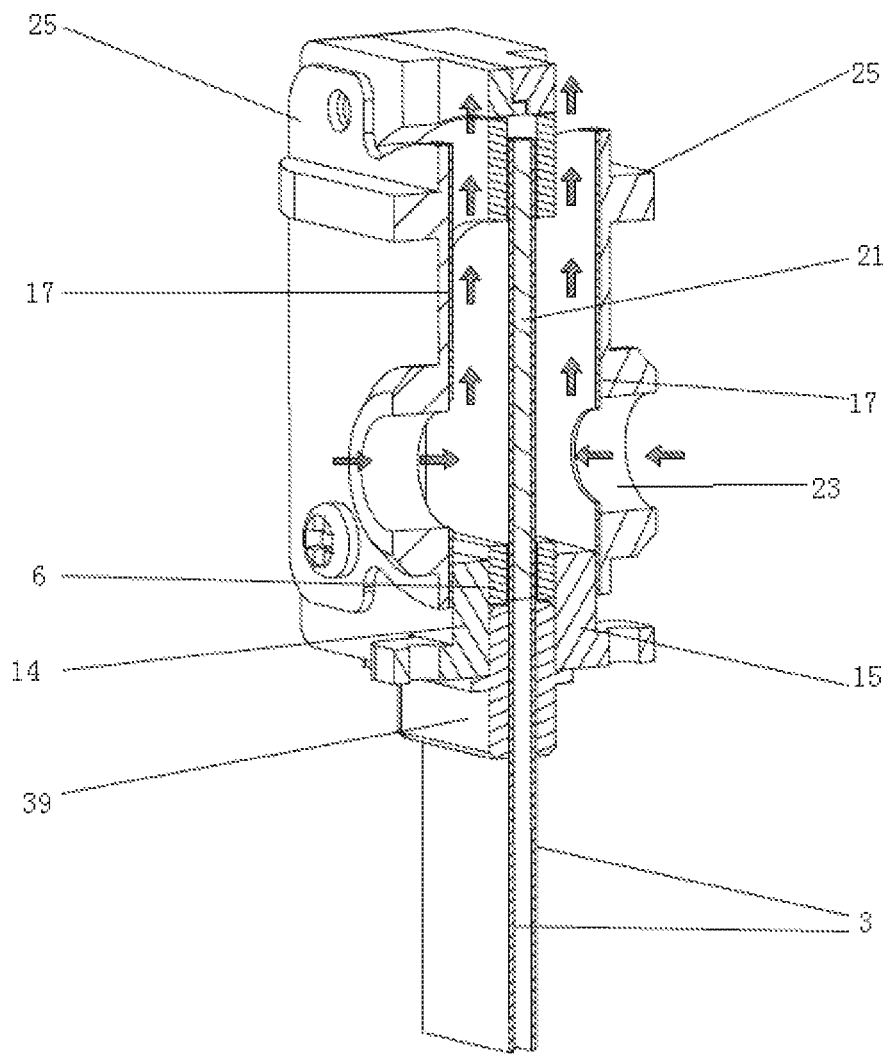
FIG. 5 is a structural schematic diagram of an atomization core in embodiment 2 of the present invention.
Figure 6:
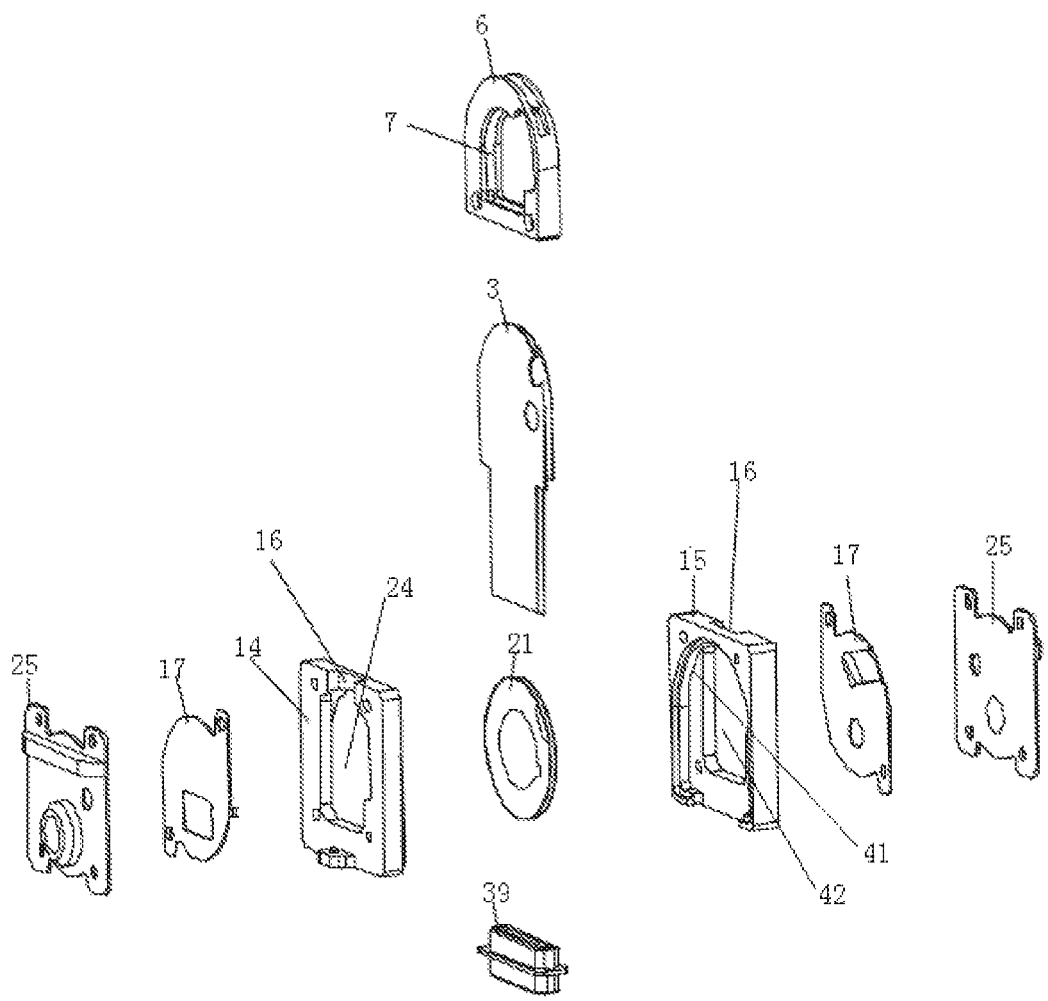
FIG. 6 is an explosive view of the atomization core in embodiment 2 of the present invention.

As shown in FIG. 5 and FIG. 6, in the embodiment 2 of the present invention, the atomization core part comprises an elastic mounting sleeve 6 provided in the outer sleeve 4; an accommodation groove 7 for accommodating the piezoelectric ceramic piece 21 and the liquid storage body 3 is provided in the elastic mounting sleeve 6; and the liquid storage body 3 covers two sides of the piezoelectric ceramic piece 21, and then a component consisting of the liquid storage body 3 and the piezoelectric ceramic piece 21 is clamped in the accommodation groove 7. A first outer cover 14 and a second outer cover 15 for fixing the elastic mounting sleeve 6 are respectively provided on one side and the other side of the elastic mounting sleeve 6; and vent grooves 16 are provided in both of the first outer cover 14 and the second outer cover 15, and the vent grooves 16 in the first outer cover 14 and the second outer cover 15 are respectively communicate with the first vent passage 51 on one side of the piezoelectric ceramic piece 21 and the second vent passage 52 on the other side of the piezoelectric ceramic piece 21.

Electrode piece mounting holes 24 are provided in both of the first outer cover 14 and the second outer cover 15. During installation, electrode pieces 17 are fixed in the electrode piece mounting holes 24 by silica gel pads, gaps enabling the gas to pass are respectively provided between the two side of the piezoelectric ceramic piece 21 and the corresponding electrode slices 17, the gaps are the first vent passage 51 and the second vent passage 52, the liquid in the liquid storage body 3 is atomized into smoke when the piezoelectric ceramic piece 21 works, and the smoke is brought into the oral cavity of the user by the airflow passing through the first vent passage 51 and the second vent passage 52.

The first outer cover 14 and the second outer cover 15 are respectively in fixed connection with one side and the other side of the elastic mounting sleeve 6, one silica gel pad is placed on each of the outer sides of the first outer cover 14 and the second outer cover 15, and the above-mentioned component is fastened by screws.

When the atomization core is fixed in the outer sleeve 4, a silica gel base 39 can be used for isolating the atomization core from the top end of the liquid storage cavity, so that shock absorption can be achieved while the leakage of the tobacco tar can be prevented.

In the embedment, the elastic mounting sleeve 6 is made of silica gel so as to prevent the piezoelectric ceramic piece 21 from being damaged in the oscillation process and prolong its working life.

In the embedment, the bottom end (one end that is away from the suction nozzle) of the liquid storage cavity 1 is fixed to a base 37, a tobacco tar injection plug 38 is provided in the base 37, the tobacco tar injection plug 38 passes through the bottom cover 20, and when the tobacco tar needs to be injected, the tobacco tar can be injected just by taking off the tobacco tar injection plug.

Figure 7:
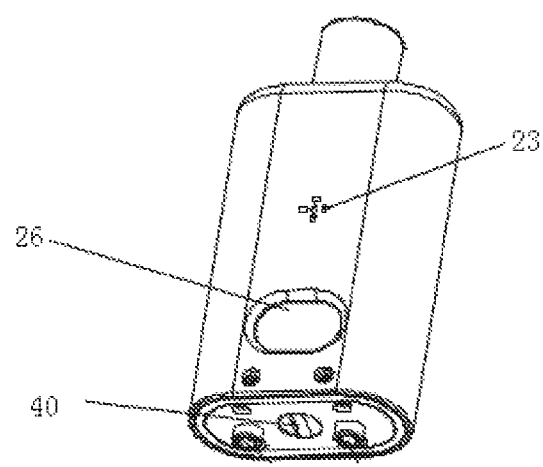
FIG. 7 is a schematic diagram of an external structure of an atomizer in embodiment 2 of the present invention.

As shown in FIG. 7, in the embodiment 2, an observation window 26 is provided in the outer sleeve 4 to conveniently observe whether the tobacco tar in the liquid storage cavity needs to be supplemented, and a tobacco tar inlet hole 40 is provided in the bottom cover to facilitate injection of the tobacco tar.

Figure 8:
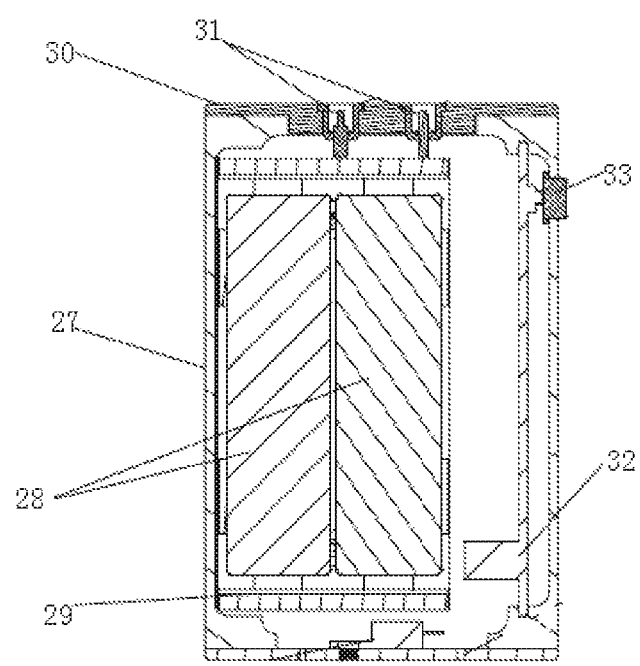
FIG. 8 is a structural schematic diagram of a power supply component of the present invention.

FIG. 8 is a structural diagram of a power supply component of the present invention. The power supply component comprises a box 27, a lithium battery 28 is fixed in the box 27 by a battery bracket 29, a power supply spring electrode 31 insulated from an upper cover 30 is fixed to the upper cover 30 of the box 27, and the power supply spring electrode 31 is in contact with the lithium battery 28. A control board 32 is vertically provided in the box 27, a key 33 is fixed to one side of the box 27, and the key 33 is in electrical connection with the control board 32.

When in use, the bottom cover 2C) of the atomizer is in threaded connection, magnetic connection or plug connection with the upper cover 30 of the power supply component.

The invention claimed is:

1. An ultrasonic atomizer, wherein the ultrasonic atomizer comprises a liquid storage cavity, an ultrasonic oscillation component and an air passage provided in an outer sleeve, and an electrode electrically connected with an external power supply for driving oscillation of the ultrasonic oscillation component; the ultrasonic oscillation component comprises a piezoelectric ceramic piece and a liquid storage body; the piezoelectric ceramic piece is provided to extend along the longitudinal direction of the ultrasonic atomizer; at least one surface of the piezoelectric ceramic piece is in contact with the liquid storage body; the liquid storage body communicates with the liquid storage cavity; and the liquid storage body communicates with the air passage.

2. The ultrasonic atomizer of claim 1, wherein the liquid storage cavity and the piezoelectric ceramic piece are provided side by side.

3. The ultrasonic atomizer of claim 2, wherein the ultrasonic atomizer further comprises a side cover; the side cover is covered on one side of the outer sleeve; an accommodation cavity is provided in the side cover; and the piezoelectric ceramic piece is provided in the accommodation cavity.

4. The ultrasonic atomizer of claim 3, wherein the ultrasonic atomizer further comprises a bracket and a fixing base; a cavity for accommodating the ultrasonic oscillation component is provided in the fixing base, the ultrasonic oscillation component is fixed in the fixing base, and the fixing base is embedded in the accommodation cavity through the bracket.

5. The ultrasonic atomizer of claim 4, wherein a first vent groove is provided in the bracket, a second vent groove is provided in the fixing base, and both of the first vent groove and the second vent groove communicate with the surface of the liquid storage body which is deviated from the piezoelectric ceramic piece.

6. The ultrasonic atomizer of claim 1, wherein the piezoelectric ceramic piece is provided above the liquid storage cavity.

7. The ultrasonic atomizer of claim 6, Wherein both sides of the piezoelectric ceramic piece are in contact with the liquid storage body, and the surface of the liquid storage body which is deviated from the piezoelectric ceramic piece communicates with the air passage.

8. The ultrasonic atomizer of claim 6, wherein an elastic mounting sleeve is provided in the outer sleeve; an accommodation groove for accommodating the piezoelectric ceramic piece and the liquid storage body is provided in the elastic mounting sleeve, and the wall of the accommodation groove is in elastically contact with the piezoelectric ceramic piece and the liquid storage body.

9. The ultrasonic atomizer of claim 8, Wherein a first outer cover and a second outer cover for fixing the piezoelectric ceramic piece are respectively provided on one side and the other side of the elastic mounting sleeve; and vent grooves communicating with the air passage are provided in both of the first outer cover and the second outer cover, and the vent grooves respectively communicate with the air passage on one side and the other side of the piezoelectric ceramic piece.

10. The ultrasonic atomizer of claim 9, wherein a first through hole is provided in the middle of the first outer cover, a fixing groove is provided in one surface of the second outer cover which is faced to the first outer cover, the piezoelectric ceramic piece is provided in the fixing groove, and a second through hole is provided in the wall of the fixing groove which is faced to the first through hole; and the first through hole and the second through hole are respectively provided on one side and the other side of the piezoelectric ceramic piece and both of them communicate with the air passage through the vent grooves.

11. The ultrasonic atomizer of claim 10, wherein sealing pads are provided on the surface of the first outer cover and on the surface of the second outer cover which are deviated from the piezoelectric ceramic piece, and gaps are provided between the sealing pads and the surface of the liquid storage body which is deviated from the piezoelectric ceramic piece.

12. The ultrasonic atomizer of claim 1, wherein one end of the outer sleeve is connected with a suction nozzle, and the suction nozzle communicates with the air passage.

13. The ultrasonic atomizer of claim 11, wherein one end of the liquid storage body which is away from the suction nozzle is inserted into the liquid storage cavity.

14. The ultrasonic atomizer of claim 1, wherein the liquid storage body is located on the surface of the piezoelectric ceramic piece, and the surface of the liquid storage body which is deviated from the piezoelectric ceramic piece communicates with the air passage.

15. The ultrasonic atomizer of claim 12, wherein the liquid storage body is made of a tobacco tar absorption material and is of platy structure, and the liquid storage body is provided on the piezoelectric ceramic piece.

16. Electronic cigarette, wherein the electronic cigarette comprises the ultrasonic atomizer of claim 1 and a power supply component for providing a working power supply for the ultrasonic atomizer.

17. The electronic cigarette of claim 16, wherein the ultrasonic atomizer is in screw joint, plug connection or magnetic connection with the power supply component.

* * * * *